United States Patent
Landers et al.

(10) Patent No.: US 7,534,623 B2
(45) Date of Patent: May 19, 2009

(54) APPARATUS AND METHOD FOR THE PURIFICATION OF NUCLEIC ACIDS

(75) Inventors: James P. Landers, Charlottesville, VA (US); Pamela E. Norris, Charlottesville, VA (US); Mary E. Power, Waterloo (CA); Jerome P. Ferrance, Charlottesville, VA (US); Sushil Shrinivasan, Charlottesville, VA (US); Kelley A. Wolfe, Downingtown, PA (US); Michael C. Breadmore, Margate (AU)

(73) Assignee: University of Virginia Patent Foundation, Charlottesville, VA (US)

( * ) Notice: Subject to any disclaimer, the term of this patent is extended or adjusted under 35 U.S.C. 154(b) by 715 days.

(21) Appl. No.: 10/517,980

(22) PCT Filed: Jun. 11, 2003

(86) PCT No.: PCT/US03/18403

§ 371 (c)(1),
(2), (4) Date: Dec. 13, 2004

(87) PCT Pub. No.: WO03/104774

PCT Pub. Date: Dec. 18, 2003

(65) Prior Publication Data

US 2006/0084185 A1      Apr. 20, 2006

Related U.S. Application Data

(60) Provisional application No. 60/387,794, filed on Jun. 11, 2002.

(51) Int. Cl.
*G01N 1/18* (2006.01)
*B01L 11/00* (2006.01)
(52) U.S. Cl. .......................... 436/177; 422/101
(58) Field of Classification Search .............. None
See application file for complete search history.

(56) References Cited

U.S. PATENT DOCUMENTS 6,235,471 B1 *   5/2001   Knapp et al. ................... 435/6

OTHER PUBLICATIONS

Q. Tang and M.L. Lee, Journal of Chromatography A, 887:265-275, 2000.*
S. Sato, et al., Journal of Materials Science 25:4880-4885, 1990.*
L.A. Christel, et al., Journal of Biomechanical Engineering 121:22-27, 1999.*

* cited by examiner

*Primary Examiner*—Yelena G Gakh
*Assistant Examiner*—Timothy G Kingan
(74) *Attorney, Agent, or Firm*—Blank Rome LLP

(57) ABSTRACT

The present invention is directed to novel device comprising a sol-gel filled microchannel and methods for purifying nucleic acids from biological samples. In one embodiment shown in FIG. 1, the microfluidic device (1) comprises a base (2) with a microchannel (3) formed in the interior of base (2), wherein said microchannel (3) is filled with a sol-gel matrix and in fluid communication with an inlet port (4) and outlet port (5) wherein inlet port (4) and outlet port (5) are formed on the exterior surface (10) of base (2). The device may be further provided with additional components to allow for analytical analysis of the purified nucleic acid sequences.

5 Claims, 7 Drawing Sheets

APPARATUS AND METHOD FOR THE PURIFICATION OF NUCLEIC ACIDS

RELATED APPLICATION

This application is a national stage filing of International Application Ser. No. PCT/US03/18403, filed on Jun. 11, 2003, which claims benefit under 35 USC §119(e) from U.S. Provisional Application Ser. No. 60/387,794, filed Jun 11, 2002, the disclosures of which are hereby incorporated by reference herein in their entirety.

Statement Regarding Federally Sponsored Research or Development

This invention was made with United States Government support under Grant No. HG 01832 awarded by the National Institutes of Health. The United States Government has certain rights in the invention.

BACKGROUND

Miniaturization of analytical methods and instrumentation for biomedical and clinical research is an area of burgeoning interest. In many cases, the reduction in size of an analytical procedure or technique often translates to a reduction in analysis time and costs. Miniaturization of analytical methods often paves the way for the use of established technologies in high-throughput applications. Great efforts have been made to develop fast, cost-effective, high-throughput separation methods for nucleic acid analysis. For example, microchip technology is currently being developed in which rapid thermocycling and electrophoretic separation can be accomplished 10 times quicker than conventional techniques. The microchip platform has the potential for integrating sample pretreatment, target amplification, and detection in a single device. Combination of these processes into a single device (i.e., create the elusive "lab-on-a-chip") can minimize sample loss and contamination problems as well as reduce analysis times substantially.

Purification of nucleic acids from biological sources, while commonplace, is not a trivial challenge. For example, one of the simplest sources of human genomic DNA is white blood cells (WBCs). One microliter of whole blood contains ~5000 WBCs which, in turn, contain a total of ~35 ng of DNA. While effective PCR for molecular biological analysis requires only a few copies of the genome, the more efficient the recovery of DNA, the more effective the PCR amplification. Efficient capture and purification of DNA can be affected by the presence of several PCR inhibitors in whole blood (e.g., heme from hemoglobin) as well as the numerous other components present including lipids, proteins, small ions and peptides. For this reason, purification of DNA from such systems is nontrivial.

While the functional integration of sample preparation, DNA amplification, and sample analysis in a single electrophoretic microchip has obvious advantages, the potential of a miniaturized DNA purification method extends beyond reducing analysis time in molecular diagnostics. A miniaturized DNA purification method would have further utility in a number of other areas including separating PCR product from reaction by-products, purifying DNA fragments prior to sequencing, and desalting primers of DNA hybridization targets. An effective miniaturized DNA sample preparation methodology could also be interfaced with conventional capillary electrophoresis, integrated electrophoretic microchips or pipettes capable of micro-solid-phase extraction (μSPE).

An optimal miniaturized DNA purification protocol will accomplish extraction and purification of DNA in as few steps as possible and should minimize solvent volume, lower dilution effects, and reduce the possibility of contamination.

Although methods that exploit the proclivity of certain materials for adsorbing DNA (e.g., silica, glass fibers, anion exchange resins and modified magnetic beads) have been developed for purifying DNA, little information is available regarding the design and operation of a miniaturized DNA purification method based on silica resins. Specific problems associated with μSPE devices include the total capacity of the μSPE device, the compatibility of the retained DNA fraction with PCR applications, and the reproducibility of the DNA extraction method with complex clinical samples.

SUMMARY OF EMBODIMENTS

The present invention is directed to a silica-based μSPE and the use of such a device for purifying nucleic acid sequences from complex mixtures. In one embodiment a device and method are provided for isolating RNA and DNA from biological samples, including human tissues. In a further embodiment the silica-based μSPE device is fully integrated with PCR and/or electrophoretic separation capabilities.

BRIEF DESCRIPTION OF THE DRAWINGS

FIG. 1A is a top view of a microfluidic device comprising a microchannel containing a sol-gel matrix. FIG. 1B is a cross sectional view of the microfluidic device demonstrating the location of the microchannel and the inlet and outlet ports.

FIG. 2A is a top view of a microfluidic device comprising two microchannels, one of which contains a sol-gel matrix. FIG. 2B is a cross sectional perspective view of the device through line 2A-2A of FIG. 2A.

DETAILED DESCRIPTION OF EMBODIMENTS OF THE INVENTION

Definitions

Figure 1A:
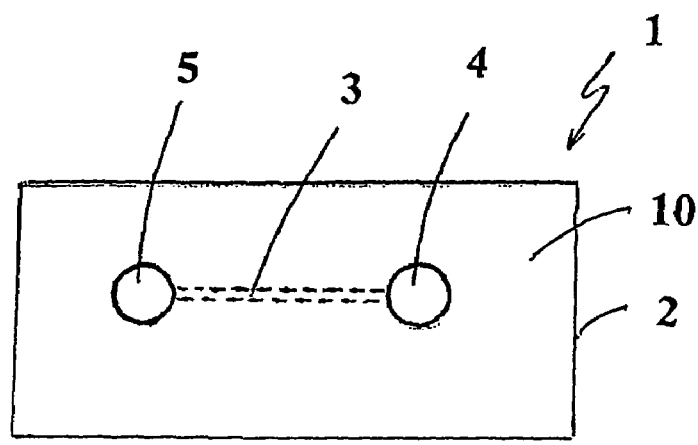
FIG. 1A & 1B.

In describing and claiming the invention, the following terminology will be used in accordance with the definitions set forth below.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

A "chaotropic agent" as used herein is an agent that is capable of disrupting the membranes or other structural components of living organisms and includes but is not limited to urea, guanidine hydrochloride, potassium iodine, enzymes such as lysozyme, alkali solutions, chelators such as EDTA and EGTA and detergents such as SDS, Tween, TritonX and Sarkosyl.

As used herein, the term "immobilization" refers to the attachment or entrapment, either chemically or otherwise, of material to another entity (e.g., a solid support) in a manner that restricts the movement of the material.

As used herein a "microcolumn" is a matrix comprising pores of a size selected form a range of about 1 μm to about 15 μm in diameter, and wherein the microcolumn has an average cross sectional dimension selected form a range of about 50 mm$^2$ to about 100 μm$^2$.

As used herein a "microchannel" is a passageway (in any form, including a closed channel, a capillary, a trench, groove or the like) formed on or in a microfluidic substrate (a chip, bed, wafer, laminate, or the like) having at least one region with a cross sectional dimension selected from a range of about 50 mm$^2$ to about 100 μm$^2$.

A "microfluidic device" is an apparatus or component of an apparatus that includes at least one microchannel.

As used herein, the term "sol-gel" refers to preparations composed of porous metal oxide glass structures. The phrase "sol-gel matrices" refers to a solid bonded network of silica prepared by a hydrolysis—condensation polymerization reaction of suitable monomers. The materials used to produce the sol-gel can include, but are not limited to, aluminates, aluminosilicates, titanates, ormosils (organically modified silanes), and other metal oxides.

Embodiments

The present invention is directed to a device and method for purifying nucleic acids from complex mixtures, including biological samples derived from living organisms. In accordance with one embodiment a microfluidic device, and a method of using that device for solid phase extraction of nucleic acids from complex mixtures, is provided. The devices described in the present invention allow for the rapid purification of nucleic acid sequences from a variety of complex mixtures including in vitro enzymatic reactions as well as from complex biological sources. For example, the present devices can be used for separating PCR product from reaction by products, purifying DNA fragments prior to sequencing, desalting primers of DNA hybridization targets, separating labeled nucleic acids from unincorporated label as well as for purifying and/or concentrating nucleic acids from prokaryotic or eukaryotic cells.

In accordance with one embodiment, the device of the present invention comprises a silica based microcolumn. In one embodiment the microcolumn is formed as a sol-gel matrix. The preparation of sol-gel matrices has been previously described by others (see Brinker, C. J., Scherer, G. W., Sol-Gel Science, Academic Press, San Diego (1990) and U.S. Pat. Nos. 5,292,801 and 5,300,564, the disclosures of which, as they relate to sol-gel synthesis, are incorporated herein). Typically a sol-gel is prepared by room-temperature polymerization of suitable monomers, usually metal alkoxides, to form a bonded network of glassy material. In accordance with one embodiment of the present invention, the preparation of sol-gels is modified to produce sol-gel matrices comprising pore sizes anywhere from about 1 μm to about 10 μm in diameter. This sol-gel matrix is formed in the shape of a column that has a cross sectional dimension ranging from about 50 mm$^2$ to about 100 μm$^2$. In one embodiment the sol-gel matrix is prepared using tetramethoxy orthosilicate (TMOS) monomers, and in a further embodiment the sol-gel is polymerized in the presence of poly(ethylene oxide) (PEO). Surprisingly, applicants have found that TMOS based sol-gels have superior properties (relative to tetraethoxysilane (TEOS) based sol-gels) in terms of column durability, consistency and efficiency for nucleic acid extractions when used as the sole component of the sol-gel matrix in the microfluidic devices.

In another embodiment the sol-gel matrix of the microcolumn comprises silica particles immobilized in a sol-gel matrix. The sol-gel matrix provides a "glue" that holds the silica particles in place, while the particle help to strengthen the column and prevent cracking. The silica particles used in the present invention can be spherical or irregular in shape and range in size from about 30 μm to about 2.5 μm, and in one embodiment the silica particles used range in size from about 15 μm to about 5 μm and in one typical embodiment the average size of the silica particles is approximately 5 μm or smaller. The column is typically prepared by inserting the sol-gel fluid into a microchannel of a microfluidic device and allowing the formation of the sol-gel matrix in the microchannel.

Accordingly, one aspect of the present invention is directed to a microfluidic device comprising a body structure that is provided with a microchannel filled with a sol-gel matrix. More particularly, the microchannel of the device is in fluid communication with an inlet port and an outlet port that are formed on an exterior surface of the body structure, thus forming a continuous passageway from the exterior surface of the device through the microchannel and back out to the exterior surface of the device. The sol-gel matrix is contained within the microchannel and spans a cross sectional dimension of the microchannel, so that a fluid traversing from the inlet port to the outlet port must pass through the sol-gel matrix. The column of sol-gel matrix present in the microchannel may extend the entire length of the microchannel or it may only extend a partial length of the microchannel. Typically the sol-gel in fluid form is inserted into the microchannel and then polymerized, so the dimensions of the sol-gel matrix match the original interior space of the microchannel. In one embodiment the interior surface of the microchannel comprises functional groups that form bonds with the sol-gel matrix, resulting in the matrix being bound to the microchannel. In one embodiment the sol-gel matrix is covalently bound to the interior surface of the microchannel, and the matrix and has pores of a size anywhere from about 0.1 µm to about 10 µm in diameter, and in one embodiment the average pore size of the matrix is about 1 µm to about 10 µm in diameter.

The device can be further provided with a reaction chamber that is situated between, and in fluid communication with, one end of the microchannel and the outlet port. The reaction chamber comprises a space to collect fluids after they pass through the microchannel and thus provides a space for further manipulation of the extracted nucleic acid sequences without requiring the removal (and potential sample loss or contamination) of the extracted nucleic acid sequences. In accordance with one embodiment additional reagents are added to the reaction chamber including for example, buffered solutions, enzymes, nucleotides, to allow for analysis of the extracted nucleic acid sequences.

In one embodiment, the reaction chamber is fitted with a removable vessel that can be inserted and removed through the outlet port. The vessel, when inserted, is placed in fluid communication with the microchannel in such a manner that fluids passing through the microchannel will be collected in the vessel. In this manner the nucleic acids can be extracted from the sol-gel matrix and washed into the vessel. The vessel can then be removed for storage or further testing without requiring further handing of the nucleic acid sample. In one embodiment the vessel comprises a tube with a removable fitted cap, for example, the vessel may be a screw cap eppendorf tube.

The microchannel can be formed using standard microchip etching techniques, or other procedures known to those skilled in the art, to provide microchannels of varying dimensions. For example, the microchannel can be prepared to have a cross sectional space in the shape of a circle, oval, square, rectangle or other multi-sided shape. Furthermore, the microchannel can be formed to have a uniform cross sectional space extending the entire length of the microchannel or the cross sectional space may increase or decrease relative to one end of the microchannel. In one embodiment the first end of the microchannel, in closest proximity to the inlet port, has a greater diameter than the second end of the microchannel, in closest proximity to the outlet port.

Applicants have discovered that microcolumns formed from silica particles alone are problematic due to compression of the particles during use, leading to high variability of column performance and failure of the columns due to clogging. To overcome the disadvantages associated with microcolumns formed solely by silica particles, a hybrid microcolumn can be formed comprising a sol-gel matrix with silica particles immobilized within the sol-gel matrix. In accordance with one embodiment a silica particle based microcolumn is prepared wherein a microcolumn of silica particles is first prepared. The silica particles column is then contacted with fluid sol-gel, and the sol-gel is subsequently polymerized. The resulting sol-gel matrix immobilizes the silica particles within the microchannel to optimize the performance of the column. Furthermore, the addition of silica particles to the sol-gel matrix has the added benefit of imparting mechanical strength to the gel.

Figure 1B:
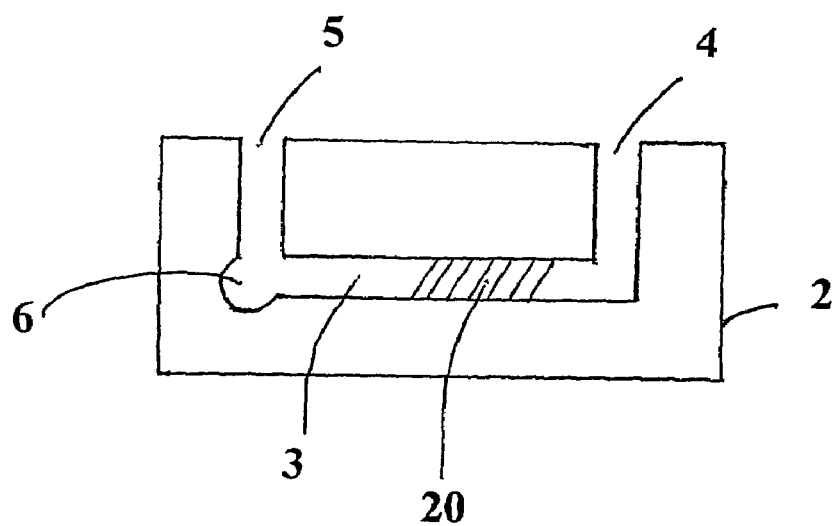

As shown in FIG. 1A, one embodiment of the microfluidic device 1 of the present invention comprises a base 2 (typically a microchip), having an upper surface 10. Base 1 has a microchannel 3 formed in the interior of the base 2 and an inlet port 4 and outlet port 5 formed on the upper surface 10 and in fluid communication with microchannel 3. The microfluidic device 1 is optionally provided with a reaction chamber 6 situated between, and in fluid communication with, microchannel 3 and outlet port 5. A cross sectional view of the microfluidic device 1 shown in FIG. 1A is shown in FIG. 1B. FIG. 1B demonstrates that microchannel 3 is at least partially filled with a sol-gel matrix 20. Sol-gel matrix 20 spans a cross sectional dimension of the microchannel, so that a fluid traversing from the first port 4 to chamber 6 must pass through sol-gel matrix 20.

To prepare the microfluidic device of the present invention a sol-gel precursor mix is prepared by hydrolyzing a suitable silica-based substrate in an acidic or basic aqueous solution, in accordance with procedures known to those skilled in the art. In one embodiment, the sol-gel is prepared from TMOS. The hydrolyzed precursor mix is then introduced into a microchannel using either positive or negative pressure. Microchips comprising one or more microchannels can be prepared using silica-based substrates and standard techniques (such as photolithographic techniques) known to those skilled in the art. In one embodiment, the microchannel is conditioned before the hydrolyzed sol-gel precursor mix is added. Conditioning of the microchannel comprises the steps of contacting the interior surface of the microchannel with a basic solution, such as 1 M NaOH, rinsing with an alcohol solution, such as ethanol, and allowing the microchannel to dry.

For construction of a microcolumn comprising a silica particle/sol-gel hybrid matrix, a temporary retaining frit was first constructed in the outlet port. In one embodiment, the frit is prepared by inserting a mixture of particles and sol-gel into the outlet port and filling the rest of the microchannel with water. The sol-gel fluid is allowed to harden forming a porous material that acts as a frit to retain silica particles subsequently introduced into the microchannel. However, any porous material can be secured to one end of the microchannel, or in one of the two ports, and used to provide functionality similar to the frit. The microchannel is then filled with silica particles under positive or negative pressure and the surface of the particles is conditioned with HCl to enable sufficient binding of the sol-gel matrix to the surface of the particles. Finally, the channel is filled with a sol-gel mixture and the sol-gel is hardened, forming a solid-silica network bound to the microchannel wall and the silica particles. The sol-gel matrix is optionally exposed to thermal treatment to assist in the polymerization of the matrix.

The resulting microfluidic device provides a rapid and efficient means of extracting RNA or DNA from biological samples. In accordance with one embodiment a method of extracting nucleic acids, and more particularly DNA, from a biological sample comprises a first step of contacting the biological sample with a chaotropic agent to lyse cellular membranes and release the cellular nucleic acid sequences. In one embodiment, the chaotropic agent comprises guanidine hydrochloride solution and in another embodiment the chaotropic agent comprises 6M guanidine hydrochloride and a detergent, such as triton X-100. After treating the biological sample with the chaotropic agent the sample is directly loaded onto a microcolumn comprising a sol-gel matrix, under conditions conducive for nucleic acid binding to the column. In accordance with one embodiment the sol-gel column comprises a matrix that has a cross sectional dimension selected from the range of about 50 mm$^2$ to about 100 µm$^2$. In one embodiment the sol-gel matrix is formed to have an average cross sectional dimension ranging from about 12 mm$^2$ to about 100 µm$^2$, wherein the matrix has an average pore size of about 1 µm to about 10 µm in diameter. The column is then washed with a suitable solvent to remove non-bound material and the bound nucleic acid sequences are then released from the column by washing the column with an appropriate buffer known to those skilled in the art. In one embodiment the nucleic acid is released from the column by washing with a buffer that is compatible with PCR reactions, such as 1×TE buffer (89 mM TRIS, 2 mM EDTA).

In accordance with another embodiment of the present invention a microfluidic device is provided that has multiple microchannels and/or ports to allow for additional processing or analysis of the nucleic acid sequences introduced into the device. In accordance with one embodiment a nucleic acid processing system is provided that extracts nucleic acids from complex mixtures and allows for subsequent analysis of the extracted sequences. The system comprises a base, typically a microchip, that has been manufactured to contain a plurality of microchannels that are in fluid communication with one another via interconnecting chambers and a series of ports formed in the exterior surface of the base. In accordance with one embodiment, the device is provided with a first and second microchannel and an inlet port and an outlet port wherein the inlet port is in fluid communication with the first end of the first microchannel, the second end of the first microchannel is in fluid communication with the first end of the second microchannel, and the second end of the second microchannel is in fluid communication with an outlet port. In this embodiment the first microchannel contains a sol-gel matrix. The device may be further provided with pumping means to regulate the flow of fluids through the system. In one embodiment the pumping means comprises one or more syringes that are in fluid communication with the inlet port and/or outlet port. In accordance with one embodiment a third port is provided that is formed in the exterior surface of the base and is in fluid communication with the second end first microchannel and the first end of the second microchannel.

In another embodiment, a nucleic acid processing system is provided that comprises a microchip base provided with a first and second microchannel and a reaction chamber, wherein the first and second microchannel and the reaction chamber are formed within the interior of the microchip and are in fluid communication with one another. The microchip further comprises a first port formed on an exterior surface of said base and in fluid communication with the first end of the first microchannel, a second port formed on an exterior surface of said base and in fluid communication with the reaction chamber and a third port formed on an exterior surface of said base and in fluid communication with the second end of said second microchannel. The reaction chamber is located between the second end of the first microchannel and the first end of the second microchannel. A sol-gel matrix is located within the first microchannel and spans a cross sectional dimension of the first microchannel. The first, second and third ports formed on the exterior surface of the microchip base provide fluid access to the microchannels from exterior sources allowing for the introduction and removal of materials into and out of the device. In accordance with one embodiment, a syringe is attached to the device to place the contents of the syringe in fluid communication with the microchannels and/or reaction chamber of the device.

In one embodiment of the present microfluidic device, the first microchannel contains a sol-gel matrix that spans a cross sectional dimension of the microchannel, and thus provides a means of conducting solid phase extraction of nucleic acid sequences from complex mixtures inserted into the first port. The second microchannel, and/or the reaction chamber, contains reagents for analyzing the nucleic acid sequences released from the first microchannel. The device can be further provided with pumping means that regulate the flow of fluids through the device. For example syringes can be placed in fluid communication with the first and second ports to regulate the movement of fluids through the first and second microchannels as well as remove the flow through and wash solutions from the reaction chamber. The second microchamber may contain any reagent or composition that is currently used to analyze nucleic acid sequences, including antibodies, labeled nucleic acid probes, electrophoretic media and buffers. In addition reagents can be added directly to the reaction chamber to conduct enzymatic reactions such as PCR amplifications or endonuclease cleavage reactions in the reaction chamber prior to moving the extracted nucleic acids into the second microchannel.

In accordance with one embodiment, the nucleic acid processing system comprises a microchip that has been manufactured to contain a first and second microchannel wherein a first end of each microchannel is in fluid communication with a reaction chamber. The device is further provided with a first port formed on an exterior surface of said microchip and in fluid communication with the first end of said first microchannel, a second port formed on an exterior surface of said microchip and in fluid communication with the reaction chamber and a third port formed on an exterior surface of said microchip and in fluid communication with the first end of said second microchannel. In this embodiment the first microchannel is further provided with a sol-gel matrix that spans a cross sectional dimension of the microchannel. Typically the first, second and third ports are each formed on the same exterior surface of the base, however in alternative embodiments the ports can be located on different surfaces of the base. Similarly, the microchannels are typically located on the same plane relative to one another and have similar dimensions, however, the dimensions of the separate microchannels can be substantially different from one another. In addition, the first and second microchannels may have identical dimensions, but they may be located at different depths on the device (i.e. not on the same plane) relative to one another. In one embodiment the nucleic acid processing system further comprises pumping means in communication with the reaction chamber to regulate fluid flow to and from the reaction chamber. These pumping means may be separate and distinct or they may constitute the same pumping means that are connected to the device and regulate fluid flow through the first and second microchannel. The pumping means may be selected from a wide variety of commercially available mechanical pumps including HPLC pumps, systolic pumps as well as other devices used to generate positive and negative pressure including syringes, aspirators, and like devices known to those skilled in the art.

Figure 2A:
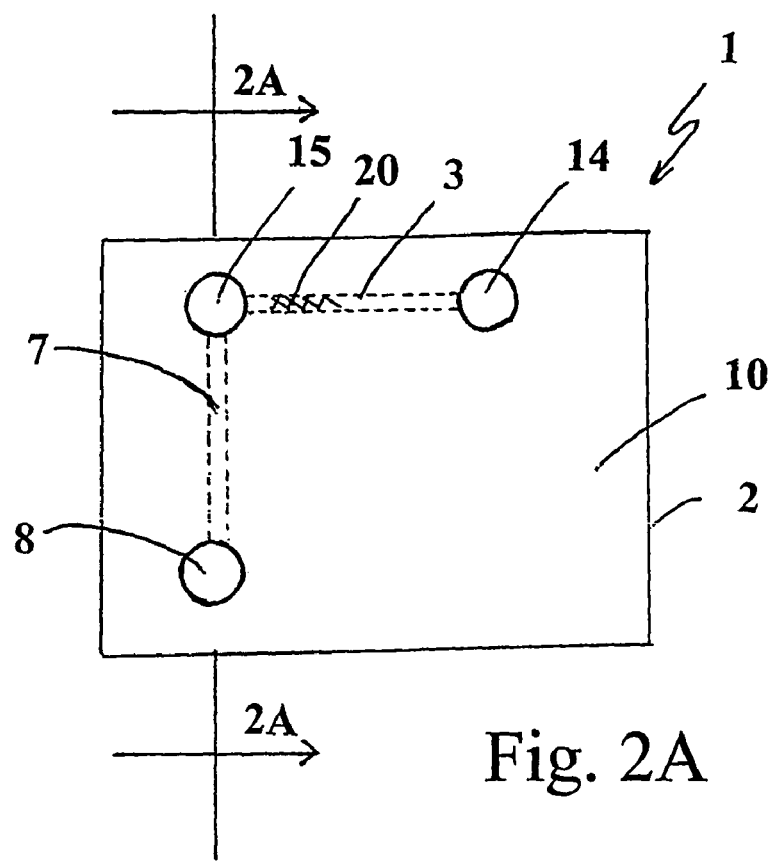
FIGS. 2A & 2B.
Figure 2B:
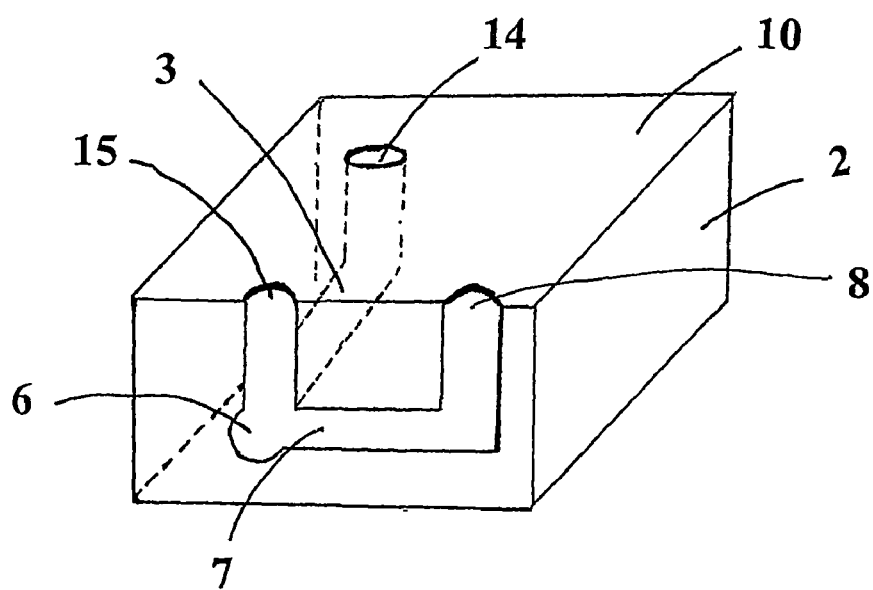

As shown in FIG. 2A a microfluidic device 1 is provided having a base 2, having an upper surface 10. Base 1 has a first microchannel 3 and second microchannel 7 formed in the interior of the base 2 with a reaction chamber 6 in fluid communication with first microchannel 3 and second microchannel 7. Base 1 is further provided with a first port 14 formed on the upper surface 10 of base 1 and in fluid communication with the first end of first microchannel 3, a second port 15 formed on the upper surface 10 of base 1 and in fluid communication with said reaction chamber 6 and a third port 8 formed on the upper surface of base 1 and in fluid communication with the second end of said second microchannel 7. As shown in the cross sectional view of FIG. 2A, microchannel 3 is at least partially filled with a sol-gel matrix 20 that spans a cross sectional dimension of the microchannel 3, so that a fluid traversing from the first port 14 to reaction chamber 6 must pass through sol-gel matrix 20.

The present invention provides an easy-to-perform protocol for DNA purification via adsorption onto a solid-support in a continuous and flow through manner. Furthermore, the method can be readily automated on a microchip format and then integrated with on-chip PCR and electrophoretic separation. In accordance with one embodiment glass microchips were prepared containing a single microchannel with dimensions 2100 μm×400 μm×60 μm.

Figure 3:
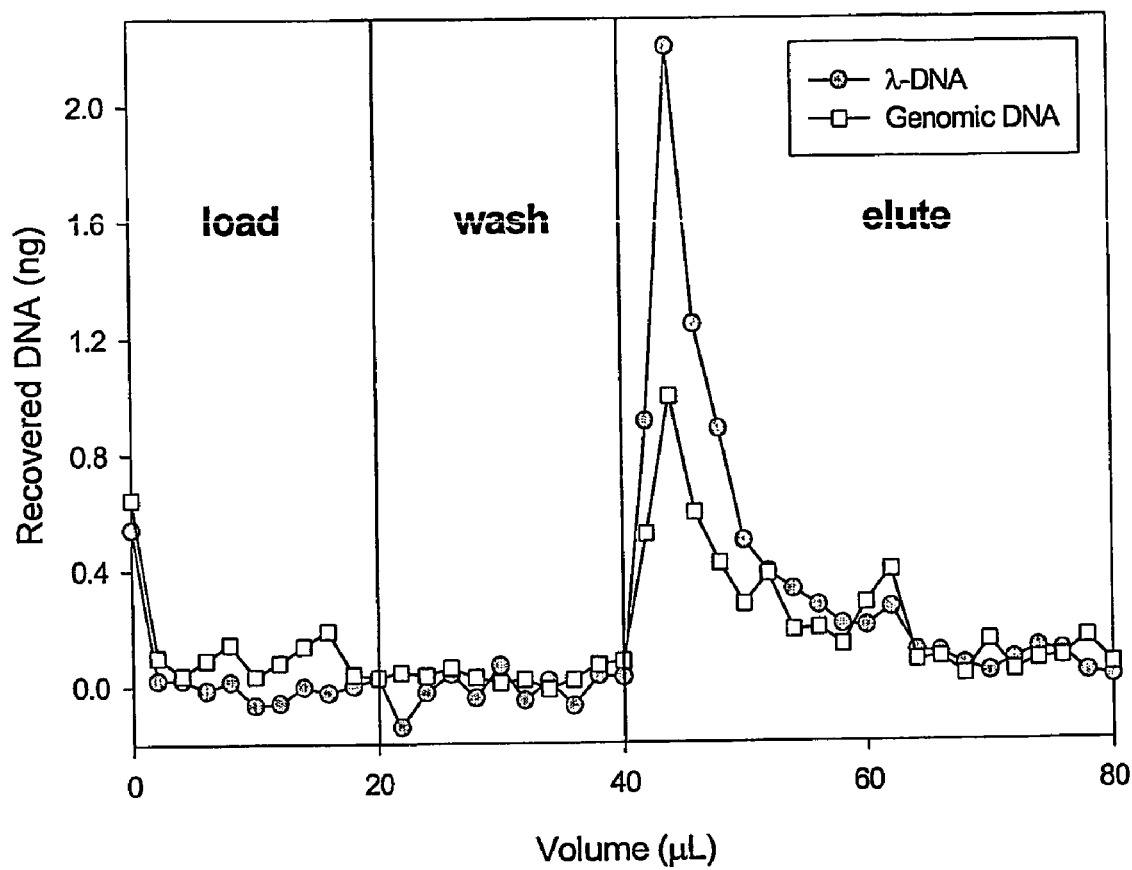
FIG. 3. Extraction profiles of λ- and genomic-DNA on μchipSPE devices. Load solution contained 500 pg/μL of either λ- or genomic-DNA in 6 M GuHCl in 1×Tris/MES buffer, pH 6.1. The flow rate for all solutions was 250 μL/h.

In accordance with the present invention the microfluidic device is used for DNA purification extraction processes. The extraction process was facilitated by connecting a syringe pump to the device using reversible low-pressure HPLC fittings and driving fluid through the silica network. Prior to use, the silica matrix is typically activated by washing the matrix with methanol and elution buffer. The extraction procedure consisted of the following steps: firstly, the silica was conditioned with a load solution comprising guanidine hydrochloride and triton X-100. Second, the sample comprising nucleic acid sequences (DNA) was mixed with the load solution and pumped through the silica phase. Third, proteins were removed by a mixed alcohol/water solution and, finally, the DNA was eluted with a buffer of suitable ionic strength and amenable to PCR amplification. FIG. 3 shows the extraction profile of λ- and genomic DNA from a bead sol-gel filled microchip. Elution of DNA from the silica matrix is typically achieved using low-ionic strength buffers at moderate pH (e.g., 1×TE [89 mM TRIS, 2 mM EDTA]). Given that the next step for integration on a microchip is PCR, elution of the DNA in a buffer not counterproductive to the PCR process is highly desirable. Furthermore, elution of the DNA with actual PCR buffer would greatly simplify the extraction process. Examination of the performance of standard TE buffer commonly used for DNA elution and PCR buffer show no difference in performance. Using these procedures, it is possible to purify DNA from clinical samples, such as blood and bacterial colonies.

To increase the potential of the purification method, it is often necessary to modify the silica surface. An easy method for surface modification is the use of polyelectrolyets. These have been used in Capillary Electrophoresis to control the surface charge and hence the direction of the electroosmotic flow and to prevent the adsorption of proteins (See Wang and Dubin, *Anal. Chem.*, 71 (1999) 3463, Córdova et al, *Anal. Chem.*, 69 (1997) 1370, Zou and Ye, *Electrophoresis*, 21 (2000) 4073, Fritz and Steiner, *J. Chromatogr. A.*, 934 (2001) 87, of which are hereby incorporated by reference herein in their entirety). The stability of the adsorbed polyelectrolyte layer can be improved by using multiple layers (See Decher, *Science* 277 (1997) 1232, Graul and Schienoff, *Anal Chem* 71 (1999) 4007, Katayama et al, *Anal Chem*, 70 (1998) 5272, of which are hereby incorporated by reference herein in their entirety). As the silica surface is negative due to the presence of silanol groups, a cationic polymer can be adsorbed and bound via electrostatic interactions, thus providing a positive surface charge. An anionic layer can be introduced by adsorption of an anionic polymer onto the cationic layer, and the process repeated successively building up polymeric layers on the silica surface. The development of such a method would allow easy surface modification in microchips, since all that is required is to flush the microchip chamber with a dilute solution of polyelectrolyte. The feasibility of this approach has been tested by applicants using capillary electrochromatograhpy, in which a capillary was filled with TMOS based sol-gel and successively coated with alternative cationic and anionic polyelectrolytes.

EXAMPLE 1

Preparation of Sol-Gels for Use in Solid Phase Extraction

Materials and Methods

Reagents

Silica beads, 15 μm and 5 μm diameter, were a gift from Mallinckrodt-Baker. Carbowax Sentry polyethylene glycol (PEG) 3350 was purchased from Union Carbide (Danbury, Conn., USA). Propyltrichlorosilane, tetraethoxysilane (TEOS), guanidine HCl, HNO3, KOH, NaOH, Tris, EDTA, 2-propanol, and HinD III digested phage DNA were purchased from Sigma-Aldrich (St. Louis, Mo., USA). PicoGreen dsDNA intercalating dye was purchased from Molecular Probes (Eugene, Oreg., USA). HCl was purchased from Fisher (Fairlawn, N.J., USA). Taq polymerase and other PCR reagents were purchased from Perkin Elmer (Santa Clara, Calif., USA). Fused-silica capillary tubing, 200 μm ID, was purchased from J&W Scientific (Folsom, Calif., USA). Borofloat glass for cover plates was purchased from S. I. Howard Glass (Worchester, Mass., USA) and borofloat glass coated with chrome and photoresist, for production of microchip devices, was purchased from Nanofilm (Westlake Village, Calif., USA). All solutions were prepared in Nanopure water (Barnstead/Thermolyne, Dubuque, Iowa, USA). TE buffer (10 mM Tris, 1 mM EDTA, titrated to pH 7.6 with HCl), 6 M guanidine-HCl in TE buffer, and 80% 2-propanol were used for the SPE procedure. Stock solutions (0.5 g/mL) of the HindIII digested phage DNA were prepared in 6 M guanidine-HCl solution and TE buffer. These were diluted as needed in the appropriate buffer for DNA adsorption experiments and for use as standards in the DNA quantitation assay.

Device Preparation

Sols were prepared by hydrolyzing a 27% v/v solution of TEOS in water by the addition of 0.1% v/v HNO3 and heating to 60° C. for 10 min then 80° C. for 60 min with stirring at 200 rpm. Gelation of the sol was carried out by the addition of 5.0% v/v of a 1 M solution of hydroxide in water for base-catalyzed condensation, or by increasing the temperature to 100° C. for condensation under acidic conditions. For slurry-type devices, the silica beads were added to the sol before condensation. All base-catalyzed sol-gels were allowed to age 24 h at room temperature and all sol-gel/bead slurries were aged at 100° C. for 1 h to facilitate ethyl alcohol evaporation and promote condensation. Capillaries were filled using positive pressure, with the packing material, either sol-gel or sol-gel/silica bead slurry, being injected from a 1 mL syringe. Microchambers were filled with sol-gel using a 1 mL syringe attached to a microchip interface. Devices incorporating silica beads and sol-gel/silica bead mixtures were filled using vacuum to draw material into the microchamber.

The microdevices themselves were prepared from borofloat glass using standard lithographic and wet etching procedures. Etched wafers and cover plates, through which access holes had been prepared, were thermally bonded at 680-695° C.

Apparatus

The SPE apparatus consisted of a Harvard Apparatus Model 22 Syringe Pump (Harvard Apparatus, Holliston, Mass., USA), and a 100 μL Hamilton gas-tight syringe (Hamilton, Las Vegas, N-V, USA). For capillary experiments the syringe was connected with a Micro-tight PEEK tubing sleeve and mini-tight fittings (Upchurch Scientific, Oak Harbor, Wash., USA) to a 40 mm long section of fused-silica capillary tubing. For microchip-based experiments the syringe was connected using 0.75 mm ID. PEEK tubing and mini-tight fittings to a noncommercial Teflon/plexiglass microchip interface.

SPE Procedure

All extraction devices were rinsed with MeOH for silica activation before use. Between extractions, the device was flushed with TE and 6 M guanidine solutions before loading the sample. A 25 µL aliquot of the phage DNA in guanidine stock solution (12.5 ng of DNA) was passed through a device at a flow rate between 100-200 µL/h. A 25 µL aliquot of 80% 2-propanol was passed through the device to remove the guanidine and contaminating substances. The DNA was then eluted from the solid phase by passing TE buffer through the device. The load and wash solutions, along with aliquots of the eluent were collected in microcentrifuge tubes and analyzed using Pico-Green intercalating dye in a TD-700 fluorometer (Turner Designs, Sunnyvale, Calif., USA). Extracted DNA samples were PCR-amplified using a Perkin Elner Thermocycler and a standard PCR protocol. All amplified samples were analyzed on the Bio-Analyzer 2100 (Agilent Technologies, Palo Alto, Calif., USA) using the DNA 500 kits according to the manufacturer's instruction.

Results and discussion

Extraction Using Silica Beads in a Microchamber

Transfer of DNA SPE procedures previously used in larger devices to a microchip is difficult due in part to the difficulty of stabilizing the beads within the chamber. Although complicated and time-consuming, Oleschuk et al. *Anal. Chem* 2000, 72 585-590, showed it was possible to use differential etching to create a structure within the microchip to retain the particles. To examine the potential of using such a structure to retain silica beads for DNA extraction, a microdevice was prepared having a 30 µm deep inlet and extraction chamber, while the outlet channel was etched only 12 µm deep. This formed a weir to prevent loss of the 15 µm silica beads used to fill the chamber. Although clogging of the inlet channel often occurred, beads could be successfully packed as a slurry in a 5% v/v glycerol/water solution using vacuum. Once packed, extraction efficiencies using these devices were found to be as high as 80%, however, extractions on the same microchip and between microchips were highly irreproducible. It was observed that as the microchip was used, the beads began to pack more tightly, causing increased backpressure, decreased flow, and varied flow patterns through the system. This led to decreased extraction over time, and was believed to be a main cause of irreproducibility. Eventual destruction of the devices was also observed as the pressure increased to the point at which shattering of the glass microchip substrate occurred. Even given the limitation of performing only a single extraction per microchip, this approach was found to be unsuitable due to the variable performance between microchips, which is believed to result from variations in the amount and arrangement of the silica beads within the packed bed.

Extraction Using a Sol-Gel Matrix

To overcome problems associated with the use of silica beads in a weir-controlled microchamber, silica sol-gel structures were created and tested for their DNA extraction ability. The condensation reaction, which produces the final network structure, can be catalyzed by the addition of base. Acid-catalyzed condensations can also be used to form the sol-gel matrix, but these reactions occur more slowly. This approach avoids many of the problems associated with packing particles into the microchip. Initial efforts to examine this approach for DNA extraction focused on filling microchip chambers with sol-gel. However, since the gel matrix cannot be removed from the device once formed, capillary devices provided a more cost-effective vehicle for initial tests. Using capillary devices, two types of TEOS-based sol-gels were investigated: hydrophilic gels, formed by the base catalyzed condensation of the sol, and more hydrophobic gels, modified by addition of propyltrichlorosilane (ITS) during gel formation. As expected, better efficiencies were obtained with the more hydrophilic material. This may be due to the small pore size in the solgel matrix (about 100 nm), which would inhibit liquid flow. Attempts to increase the size of the pores of the TEOS-based sol-gel matrices by the addition of polyethylene glycol to the sol-gel precursor solution did not significantly improve flow in the capillary devices. A further disadvantage of the sol-gel matrices was the large coefficients of variance determined for these materials.

Silica Bead/Sol-Gel Capillary Devices

Silica beads alone are problematic due to compression of the particles during use, and TEOS based sol-gels were found to be problematic due to poor mechanical stability. It seemed likely, however, that a combination of the two approaches might provide a workable system. To examine the potential of this approach for DNA extraction, 15 µm silica beads were added to the sol-gel precursor mixture to form a slurry. However, a stable suspension was not obtained due to the size of the particles and their proclivity for settling out in the devices before the matrix had completely gelled. In an effort to improve the stability of the suspension, the 15 µm beads were replaced with 5 µm silica particles, which we had determined to yield similar extraction efficiencies.

The hybrid sol-gel/silica bead matrices were created in capillaries using either a base-catalyzed or acid-catalyzed condensation step. While it was expected that both methods would perform similarly, it was surprising to find that the acid-catalyzed media performed substantially better than the base-catalyzed material. Extraction efficiencies for the acid-catalyzed matrices were comparable to that found using silica beads alone, while the base-catalyzed slurry extracted very, poorly. An additional benefit of using the acid catalyzed media was the improved reproducibility over using silica beads alone, with a decrease in the variance from 75 to 20%. The exact reason for the large difference between the acid- and base-catalyzed slurry mixtures is not known, but may related to the rate of condensation and the subsequent variation in the surface area available for extraction.

Silica Beads/Sol-Gel Microchip Devices

The above results indicate that the best approach to extract DNA for PCR amplification is to use an acid-catalyzed sol-gel precursor solution combined with silica beads. The slurry approach did not transfer well to a microfabricated device, as beads tended to quickly settle out of the slurry and clog access ports during the filling step. Additional settling occurred as the gelation reaction took place, resulting in a two-phase system and decreasing the reproducibility of the system. To alleviate the settlement of the silica particles, the particles are first packed into the system and then held together by the sol-gel.

A redesign of the microchips allowed a small silica bead/sol-gel frit to be used to contain the beads within the microchamber in place of a weir. Both the frit slurry and the final sol were allowed to gel at 100° C. for 30-60 min. The results using this approach indicate that slightly higher extraction efficiencies can be obtained compared to silica beads alone, but the reproducibility between extractions and between microchips is greatly improved with an average % RSD of 3.05. In addition, the stability of the system is dramatically increased, with no loss of extraction efficiency as was seen with the silica bead system.

Using the silica bead/sol-gel system it is clear that the entire DNA is removed from the sample load solution as it passes through the matrix and is retained during the washing step. The DNA is then eluted from the solid phase in a very small volume of elution buffer (>10 µL), with most of the DNA released immediately. This makes it ideal for integrating with microchip-based PCR, as only a small volume will have to be transferred between areas on the microchip.

EXAMPLE 2

Isolation of Nucleic Acids from Biological Sources

Materials and Methods

Reagents were obtained form the same sources as listed for Example 1. *Salmonella typhimurium* and *Bacillus anthracis*, the Sterne vaccine strain (nonencapsulated) (Colorado Sterum Co., Bolder, Colo.), were grown to appropriate levels in culture. The *Salmonella* had a final concentration of $7.08 \times 10^8$ colony forming units per milliliter (cfu/mL). The *B. anthracis* had a final concentration of $6.60 \times 10^6$ cfu/mL.

Device Preparation.

Bottom plates for the microchips were fabricated using standard photolithographic techniques and consisted of an etched channel 2.2 cm long, 60 µm deep, with a width of 400 µm at the center. A cover plate was prepared by forming access holes at each end of the channel using a 1.1-mm-diameter diamond-tipped drill bit (Crystalite Corp., Lewis Center, Ohio). A complete device was formed by thermal bonding of the etched base to the cover plate at 690° C.

Silica bead/sol-gel hybrid microdevices were, packed using the following procedure: Sols were prepared by hydrolyzing a 27% (v/v) solution of TEOS in water by addition of 0.1% (v/v) HNO3 and heating to 60° C. for 10 min and then 80° C. for 60 min with stirring at 200 rpm. A temporary frit was constructed by placing a hydrolyzed sol-gel silica bead slurry (approximately 200 mg/mL) in the outlet access hole and heating at 70° C. for 60 min to accelerate aging and drying of the gel. The channel was then filled with silica beads by drawing a bead/water slurry through the channel toward the frit by application of a vacuum. Once packing was complete, the column bed was rinsed with 1M HCl to hydrolyze the surface of the silica and the channel walls, and then the channel was filled with hydrolyzed TEOS. The filled chip was placed in an oven at 50° C., heated to 300° C. at 8° C./min, and held at this temperature for 3 h before being allowed to cool. A similar procedure can be used to prepared sol-gel matrices from hydolysized TMOS. Surprisingly, applicants have found that TMOS based sol-gels have superior properties in terms of column durability, consistency and efficiency for nucleic acid extractions when used in the microdevices of the present invention.

Apparatus

The µchipSPE apparatus consisted of a Harvard Apparatus model 22 syringe pump (Harvard Apparatus, Holliston, Mass.), with a 250-µL Hamilton gastight syringe (Hamilton, Las Vegas, Nev.). The syringe was connected to the microchip using 0.75-mm-i.d. PEEK tubing and minitight fittings (Upchurch Scientific, Oak Harbor, Wash.) with a noncommercial Teflon/plexiglass microchip interface. A second piece of tubing was secured over the outlet hole and facilitated collection of the column effluent in microcentrifuge tubes. The dead volume of the connecting tubing and the microchip chamber was less than 1 µL.

µchipSPE Extraction Procedure.

New chips were conditioned with MeOH for 30 min at a flow rate of 250 µL/h. Prior to each extraction, chips were washed with elution buffer (TE) for 30 min, followed by GuHCl load solution without DNA for a further 30 min. The extraction procedure itself consisted of load, wash, and elution steps. In the load step, 20 µL of load buffer (6 M GuHCl, 1% Triton X-100 in 1×TE buffer) containing the DNA to be extracted was passed through the device. Proteins and possible PCR inhibitors that were adsorbed onto the silica during the load step were removed by passing 20 µL of wash buffer (2-propanol/water 80/20 (v/v)) through the solid phase. Finally, the DNA was eluted in a low ionic strength TE buffer. After elution of DNA from a sample, the microchip was conditioned with load solution (without DNA) for 5 min to prepare the surface for a subsequent extraction.

The load and wash solutions, along with aliquots of the eluent, were collected in microcentrifuge tubes and analyzed using PicoGreen intercalating dye in a TD-700 fluorometer (Turner Designs, Sunnyvale, Calif.) using separate calibration curves for each solution. Extracted DNA samples were PCR amplified using a Perkin-Elmer Thermocycler (Santa Clara, Calif.) and a standard PCR protocol. This involved, for example, 95° C. for 5 min (hot start), up to 40 cycles with 94° C. for 1 min/60° C. for 1 min/72° C. for 1 min followed by extension at 72° C. for 10 min. All amplified samples were analyzed on the Bio-Analyzer 2100 (Agilent Technologies, Palo Alto, Calif.) using the DNA 500 kits according to the manufacturer's instruction.

Results and Discussion

The development of a solid-phase extraction procedure would be of immense benefit and a considerable step toward the development of a DNA diagnostic device. However, the major obstacle preventing the development of such a device relates to the creation of a suitable solid phase. The use of a weir-type approach previously disclosed by Oleschuk et al. (*Anal. Chem* 2000, 72 585-590) achieved only limited success due to compression of the packed bed during extraction. This was overcome, in accordance with one embodiment of the present invention, by immobilizing the particles by using a sol-gel to act as an "interparticle glue." Using a single microchip containing sol-gel-immobilized silica particles, it was possible to perform over 10 successive extractions, with the recovery of λ phage DNA averaging 67% (10% RSD), a significant improvement over the one or two extractions possible without sol-gel immobilization. Furthermore, the chip-to-chip reproducibility was exceptional, with an average of 68% (6% RSD) of the λ phage DNA recovered, evaluated with data from at least three extractions on 15 different immobilized silica bead microchips. When compared to channels packed with silica particles alone (TEOS based), the performance is considerably better, suggesting that inconsistent chip-to-chip results observed in the absence of immobilization stem from the dynamic nature of the packing.

Optimization of Load pH and Flow Rate

The above results illustrate the suitability of the immobilized silica bead microchip solid phase extraction devices (µchipSPE devices) for successful integration into a "micro-total analytical system" (µ-TAS) device; however, a few other criteria must be met. First, the DNA must be of sufficient quantity and quality for PCR amplification, second, the DNA must be contained in a volume suitable for microchip-based PCR, and third, the procedure must be rapid and efficient. The initial demonstration of the potential of these immobilized devices as described in Example 1 produced PCR-amplifiable DNA in an extraction volume of about 5 µL. The total extraction time of 25 min was somewhat lengthy, however, given that the PCR and separation processes can be performed in less than 5 min each. It would, therefore, be desirable to decrease the extraction time to a length similar to that possible for PCR and separation. The easiest method to decrease the extraction time is to increase the flow rate; this must be done in a manner that does not reduce DNA extraction efficiency and, therefore, requires careful examination of the DNA extraction process. Since the most critical component of the extraction process is initial adsorption of the DNA onto the silica surface, attention was focused on the load step and on ways to improve the flow rate without sacrificing DNA adsorption efficiency.

The DNA purification process employed here utilizes the adsorption of DNA onto bare silica under high ionic strength chaotropic conditions. The high ionic strength serves to shield the negative surface, reducing the electrostatic repulsion between the negative DNA and the surface of the silica, while the chaotropic salt dehydrates the silica surface and DNA, thus promoting hydrogen bonding between the DNA molecules and the protonated silanol groups. These two factors combine to allow DNA to adsorb onto silica surfaces. It has been reported that the type of salt, concentration, and pH of the solution significantly affected the adsorption of DNA onto silica surfaces. Of interest here is the significant effect of pH on DNA adsorption, with lowering the pH of the solution from 8 to 5 having two pronounced effects. First, the saturation level (DNA binding capacity) of the surface increased on decreasing the pH to 6 by at least a factor of 2, with further reduction of the pH producing no further changes in capacity. Second, the initial slope of the adsorption isotherm was much higher at pH 5 than at pH 8, indicating more rapid adsorption of the DNA onto the surface. These two effects were explained by a reduction in the extent of protonation of the silanol groups, thus reducing electrostatic repulsion between the DNA and the silica surface while also providing more protonated silanol groups capable of hydrogen bonding to the DNA.

It seemed likely that reducing the pH of the load buffer while increasing the flow rate would potentially maintain DNA adsorption, allowing a reduction in extraction time without sacrificing performance. To examine the potential of this approach, the extraction efficiency of DNA was examined using a flow rate of 250 µL/h for the load, wash, and elution steps (previous studies were performed at 150 µL/h) and three different buffers: (1) pH 7.6 (6 M GuHCl in 10 mM Tris, 1 mM EDTA, pH adjusted with HCl), (2) pH 6.1 (6 M GuHCl in 10 mM Tris, 1 mM EDTA, pH adjusted with MES), and (3) pH 4.8 (6 M GuHCl in 10 mM Tris, 1 mM EDTA, pH adjusted with acetic acid). Using the same microchip, three extractions were performed at each different pH with 53%±4%, 81%±3%, and 79%±2% of the DNA recovered for pH 7.6, 6.1, and 4.8, respectively. As anticipated, the DNA extraction performance improved as the pH decreased due to the combined increases in binding capacity and binding isotherm. Interestingly, there was no further benefit when the pH was lowered to 4.8.

Having verified that lowering the pH enabled increased flow rates through the system to be utilized, the rate was varied to determine the optimal flow rate for the different pH solutions. Given that there was essentially no difference in extraction efficiency of the DNA between buffers with a pH of 4.8 and 6.1, the lower pH buffer was not tested, as this load buffer could introduce detrimental effects relating to protein and lipid adsorption on the silica surface. While a similar profile is observed at the two different pHs, the position of the maximums occurs at the much higher flow rate of 250 µL/h when a buffer at pH 6.1 is used; at pH 7.6 it is only 175 µL/h. This translates to a total extraction time of less than 15 min at pH 6.1 compared to 25 min at pH 7.6, representing a significant reduction in extraction time. Once integrated into a total analysis device, it should be possible to perform purification, PCR amplification, and separation in less than 30 min.

Extension to Human DNA

For the µchipSPE device to be used for biological samples, it is imperative that the procedure be capable of extracting human genomic DNA fragments (>50 kb) with reasonable efficiency. To examine this, 20 µL of load solution containing 500 pg/µL λ-DNA or prepurified human genomic DNA was prepared and passed through the extraction device using the optimum procedure developed above: a pH 6.1 load solution and a flow rate of 250 µL/h. Effluent from the microchip was collected every 2 µL and assayed using the PicoGreen fluorescence method to obtain the extraction traces shown in FIG. 3. As can be seen, the extraction efficiency of DNA from the stationary phase is somewhat lower for human genomic DNA when compared to λ-phage DNA. The elution profile is almost identical for the two, however, about 80% of the eluted DNA was collected within 10 µL. The lower extraction efficiency of human genomic DNA appears to result from inefficient elution of the adsorbed DNA from the silica phase. The lack of DNA detected in the effluent load solution (FIG. 3) indicates it was not due to inefficient retention of the DNA onto the silica surface. Even given this lower extraction efficiency of DNA (50% for human genomic versus 70% for λ DNA), there was sufficient DNA obtained for PCR amplification of the β-globin gene (discussed below).

Purification of Genomic DNA from Whole Blood

Given that the eventual µ-TAS may potentially be portable and useable in a point-of-care situation, the best sample with which to test the device is whole blood. Blood serves as a stringent test of the µchipSPE purification ability, as it is a complex mixture of cells, proteins, peptides, lipids, carbohydrates, and other low molecular weight compounds that are known to inhibit the amplification of nucleic acids by PCR. To test the performance of the µchipSPE method, 10 µL of thawed frozen blood was mixed with 1000 µL of GuHCl (pH 6.1) with 1% Triton X-100. The Triton X-100 is added to help lyse the cells and solubilize organic matter and has no impact on the extraction process. The optimum procedure developed above was used for purification: 20 µL of load (6 M GuHCl, 1% Triton-X 100 in 1X TE buffer at pH 6.1), wash, and elution buffer was passed through the device at a flow rate of 250 µL/h, with each step taking about 5 min. During the elution stage, fractions were collected every 4 µL and submitted for PCR. Amplification of the 380-bp fragment of the β-globin gene, as identified by microchip electrophoresis separations, was used to indicate successful extraction and purification of the DNA.

Figure 4:
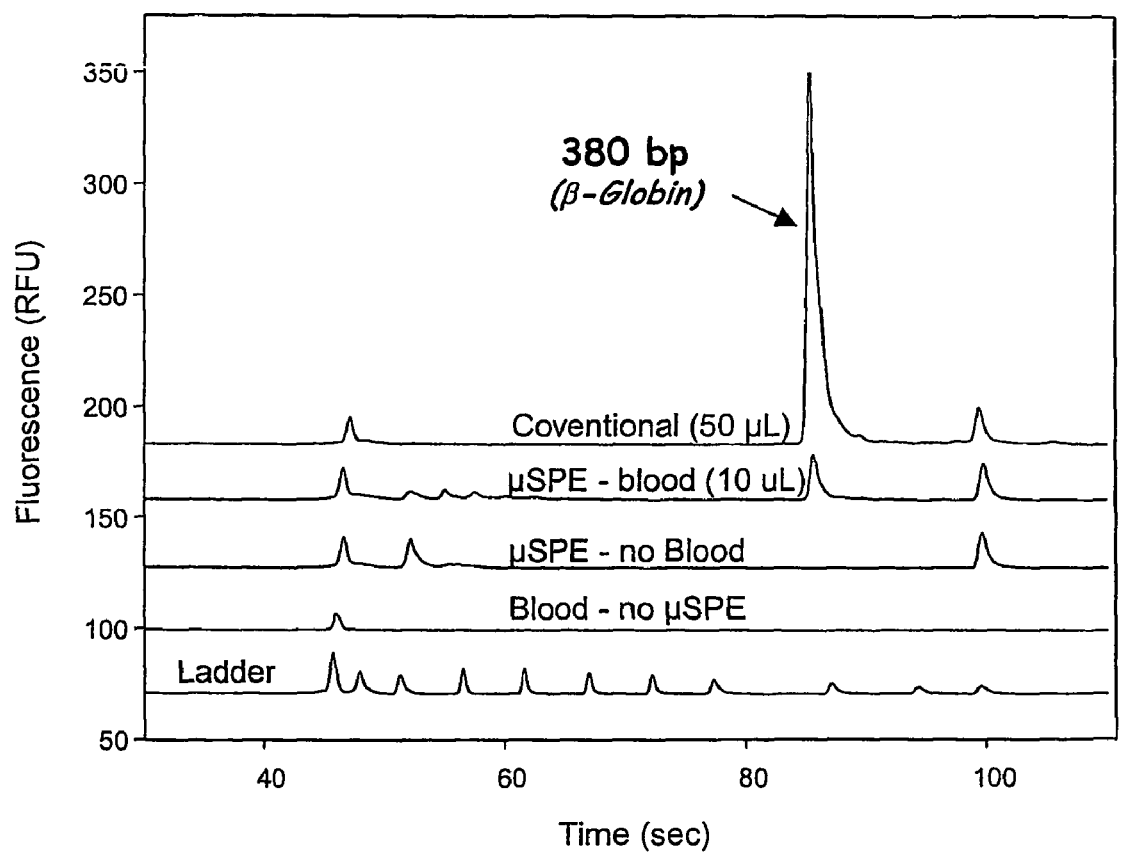
FIG. 4. Electropherograms of PCR product microchip separations after amplification of the β-globin gene in human genomic DNA. The following samples were analyzed: 2 ng of prepurified genomic DNA (50 μL) added directly to PCR mix. Approximately 10 ng of human genomic was onto the μchipSPE device and PCR performed with the second 4-μL elution fraction. As a negative control, no DNA included in the load buffer during μchipSPE, and PCR amplification was conducted on the second 4-μL elution fraction. 10 μL of whole blood added to 1 mL of 6M GuHCl and 1% Triton X 100; 20 μL of this solution loaded onto a μchipSPE device, and finally as a further negative control, 2 μL of whole blood was added directly to the amplification reaction.
Figure 5:
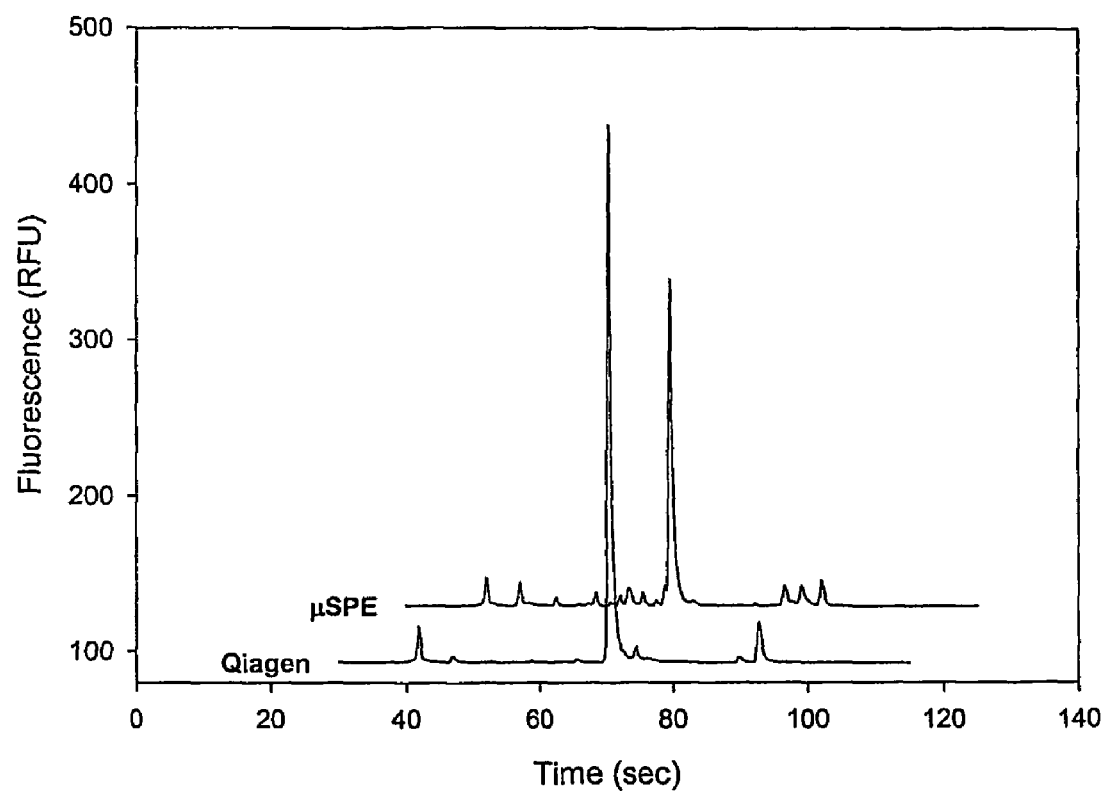
FIG. 5. PCR amplification of bacterial DNA purified from *S. typhimuiriumby* μchipSPE and a commercial purification procedure. The commercial method used 200 μL of bacterial colony and was finally reconstituted in 100 μL of elution buffer. The μchipSPE procedure used 20 μL of sample load solution (20 μL of bacterial colony in 1 mL of 6 M GuHCl, pH 6.1), loaded onto the microchip device at 250 μL/h. PCR was performed using 5 μL of reconstituted DNA solution from the commercial method or 5 μL of the second elution fraction from the microchip (about 12 μL total volume).

FIG. 4 shows the results from a positive control in which 2 ng of purified human genomic DNA was directly added to the PCR mixture and thermocycled. The same 380-bp fragment is amplified from µchipSPE of prepurified human genomic DNA, whereas the target fragment is absent when µchipSPE is carried out with no DNA loaded onto the microchip device. Microchip separation of the PCR amplification product using template DNA purified from whole blood in the µchipSPE device is also shown in FIG. 5. The presence of the 380 bp peak shows the potential of this procedure to isolate DNA from a crude matrix, such as blood, which normally would severely inhibit the PCR reaction.

It is worthy of note that, when the whole blood sample was processed, there was slight discoloration of the silica indicating absorption of the yellow heme onto the surface. This was subsequently removed as indicated by the silica turning from a pinkish hue to opaque during the wash step and by successful amplification of the β-globin gene, where even trace amounts of heme are known to be destructive.

Purification of Bacterial and Viral DNA

Having demonstrated the suitability of the μchipSPE device to purify DNA from whole blood, the full potential of the procedure was examined by comparing the extraction performance of the μchipSPE procedure with a commercial purification procedure for bacterial DNA from cultured *S. typhimurium* samples. A commercial ion-exchange based purification method (Qiagen) was carried out in a microcentrifuge tube according to the manufacturer's instructions. The procedure consists of mixing a bacterial sample with load solution, passing it through a small column by centrifugation, washing twice using ethanol with spinning after each step, and finally eluting the DNA in a suitable volume of buffer. The total time for the processes was about 30 min, using 200 μL of cultured sample (about 13.8 μg of DNA), and reconstituting the DNA in 100 μL of buffer. In contrast, the μchipSPE method involves preparing a sample load solution (20 μL of the bacterial culture in 1 mL of load buffer), passing 20 μL of this solution (about 28 ng of DNA) through the μchipSPE device, washing with 20 μL of wash buffer, and then eluting the DNA in TE buffer. Using a flow rate of 250 μL/h, the entire μchipSPE procedure was completed within 15 min. Successful DNA extractions were determined by the presence of the 275-bp amplified invA fragment using the extracted DNA as a template for PCR. This was shown by microchip electrophoresis, the results of which are presented in FIG. 5, where the μchipSPE procedure and the commercial kit produce similar size peaks for the amplified fragment. Since PCR is a nonquantitative process, the slightly less DNA in the μchipSPE trace may be related to the number of starting copies of template available for PCR but could also be due to differences in PCR efficiency. Given that the μchipSPE process requires only 400 nL of bacterial culture sample per extraction, as opposed to the 200 μL required for the Qiagen kit, and the extraction time is half that of the commercial kit, the μchipSPE procedure is ideally suited for implementation of a portable DNA diagnosis device.

Potential Application in a Portable Device

Figure 6:
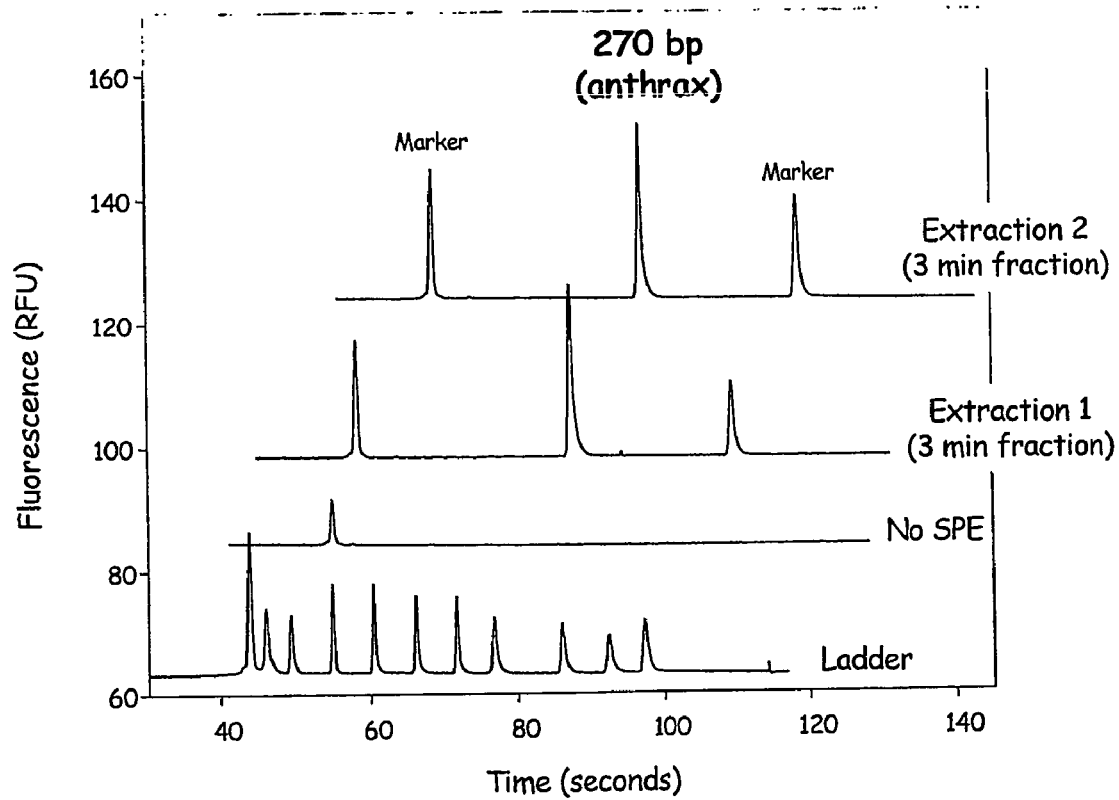
FIG. 6. Successive extractions of bacterial DNA from the vaccine strain of *B. anthracis* (anthrax) using the μchipSPE procedure. A total of 100 μL of bacterial colony was added to 500 μL of load buffer (6M GuHCl, pH 6.1); 20 μL of this solution was passed through the microchip device at 250 μL/h. PCR was performed with 5 μL of the first elution fraction (about 12 μL).
Figure 7:
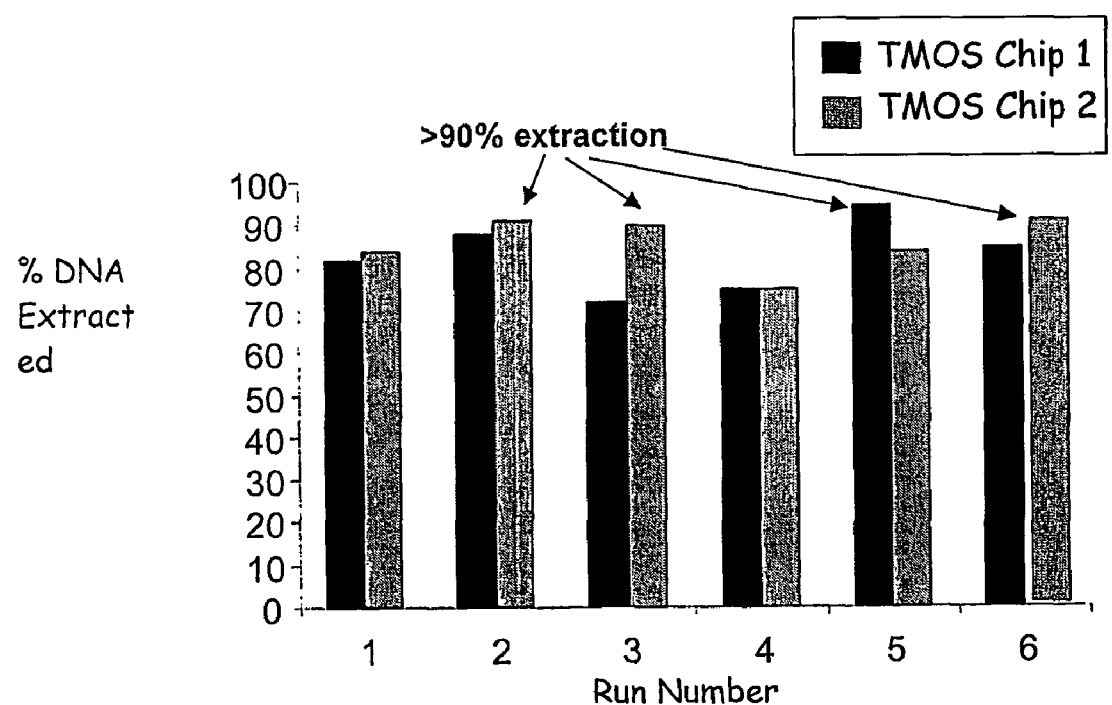
FIG. 7. is a bar graph representing data showing the recovery of λ-DNA from a TMOS monolithic microchip.

One application of a portable device would be the detection of pathogenic organisms such as *B. anthracis*. As such, purification of DNA from the anthrax virus vaccine (*B. anthracis*) is a judicious choice to determine the feasibility of the μchipSPE to aid in identifying this type of infectious agent threat. The sample was prepared by adding 100 μL of bacterial culture to 500 μL of load buffer and passing 42 μL of this sample (about 30.8 ng of DNA) through the Whip SPE device according to the developed optimum procedure. PCR was used to determine the successful purification of DNA by amplifying the 279-bp fragment of the tlf plasmid gene. Microchip electrophoresis results from two consecutive extractions are illustrated in FIG. 6, where the peak corresponding to the 279-bp fragment can clearly be seen. This, again, illustrates the suitability of this μchipSPE procedure to provide rapid purification of DNA on a microscale and its suitability for integration with on-chip PCR and separation.

The invention claimed is:

1. A method of extracting nucleic acids from a biological sample said method comprising
   contacting said sample with a chaotropic agent;
   providing a microcolumn containing a sol-gel matrix having a cross sectional dimension ranging from about 50 $mm^2$ to about 100 $\mu m^2$;
   loading the sample onto the microcolumn under conditions conducive for nucleic acid binding to the sol-gel matrix;
   washing the matrix with a solvent; and
   releasing the bound nucleic acid from the column.

2. The method of claim 1 wherein the sol-gel matrix has a cross sectional dimension ranging from about 24 $mm^2$ to about 100 $\mu m^2$.

3. The method of claim 2 wherein the nucleic acid is DNA.

4. The method of claim 2 wherein the sol-gel matrix comprises pores having a diameter selected from the range of about 0.1 μm to about 10 μm.

5. The method of claim 1 wherein the nucleic acid is released from the column by washing with a buffer that is compatible with PCR reactions.

* * * * *

UNITED STATES PATENT AND TRADEMARK OFFICE
CERTIFICATE OF CORRECTION

PATENT NO. : 7,534,623 B2 Page 1 of 1
APPLICATION NO. : 10/517980
DATED : May 19, 2009
INVENTOR(S) : James P. Landers et al.

It is certified that error appears in the above-identified patent and that said Letters Patent is hereby corrected as shown below:

At Col. 1, Item 75, the second named Inventor "Pamela E. Norris" should be changed to --Pamela M. Norris--.

Signed and Sealed this

Third Day of November, 2009

David J. Kappos
*Director of the United States Patent and Trademark Office*